United States Patent [19]

Fukunaga et al.

[11] Patent Number: 4,502,329

[45] Date of Patent: Mar. 5, 1985

[54] METHOD FOR CHECKING INSULATIVE CONDITION OF INSULATED WINDINGS USED IN ELECTRICAL APPLIANCES

[75] Inventors: Tokio Fukunaga; Akemi Futakawa; Mataichiro Kiso, all of Amagasaki, Japan

[73] Assignee: Mitsubishi Denki Kabushiki Kaisha, Tokyo, Japan

[21] Appl. No.: 477,366

[22] Filed: Mar. 21, 1983

[30] Foreign Application Priority Data

Apr. 7, 1982 [JP] Japan .................................. 57-59191
Apr. 14, 1982 [JP] Japan .................................. 57-63510

[51] Int. Cl.³ .......................... G01H 1/06; G01M 7/00
[52] U.S. Cl. ....................................... 73/573; 73/574; 73/579; 73/588
[58] Field of Search ................... 73/573, 574, 579, 588

[56] References Cited

U.S. PATENT DOCUMENTS

| | | | |
|---|---|---|---|
| 3,345,861 | 10/1967 | Heath | 73/579 |
| 3,580,056 | 5/1971 | Warner | 73/579 |
| 3,771,356 | 11/1973 | Mitchell | 73/658 |
| 4,128,011 | 12/1978 | Savage | 73/579 |
| 4,261,206 | 4/1981 | Futakawa | 73/579 |
| 4,281,547 | 8/1981 | Hinshaw et al. | 73/579 |
| 4,342,229 | 8/1982 | Massa | 73/579 |
| 4,400,980 | 8/1983 | Lepert | 73/579 |

*Primary Examiner*—Howard A. Birmiel
*Attorney, Agent, or Firm*—Oblon, Fisher, Spivak, McClelland & Maier

[57] ABSTRACT

The disclosure describes a method for checking an insulative condition of an insulated winding used in an electrical appliance comprising applying an external mechanical force to said insulated winding to give vibrating frequency to the same for its examination; detecting the frequency behavior to be generated in said insulated winding in the form of electrical signal outputs; and electrically processing the signals for judging deterioration occurred in said insulated winding.

6 Claims, 12 Drawing Figures

METHOD FOR CHECKING INSULATIVE CONDITION OF INSULATED WINDINGS USED IN ELECTRICAL APPLIANCES

This invention relates to a method and apparatus for checking the insulative condition of electrical apparatus and appliances. More particularly, it is concerned with a method and an apparatus for examining the insulative condition of various electrical apparatus and appliances, especially for an examination of windings in the electric generators, electric motors, and so forth used therein.

Heretofore, there have been known various non-destructive methods for checking the insulative condition of the insulated windings for electrical appliances, such as the checking of the percussive sound made by a hammer strike, the measurement of the tan δ characteristic, and so on. However, the checking method by the percussive (or strike) sound depends heavily on skills and knacks of the inspecting personnel, hence it cannot be evaluated quantitatively. On the other hand, the measurement of the tan δ requires temporary application of a high tension voltage to the insulated winding, with the additional inconvenience of its difficulty in determining a portion not in good condition.

The present invention has been made by paying attention to this point, and mainly aims at providing a method and an apparatus which are capable of performing objective as well as quantitative checking of the insulative condition of the electrical appliances without causing damage to the insulated article.

The present invention is a method for checking the insulative condition of the insulated winding used in the electrical appliances comprising applying an external mechanical force to said insulated winding to apply a vibrating frequency to the winding, measuring an accelerometer output and a natural frequency in said insulated winding to find variations in the natural frequency with respect to variations in the accelerometer output, or to detect a value of the natural frequency with respect to the accelerometer output to thereby judge deterioration of said insulated winding.

According to the present invention, in one aspect of it, there is provided an insulation checking method for insulated winding, comprising hitting an insulated article by a percussion member, measuring the behavior of vibration caused in said insulated article, and comparing the changes in the measured values with lapse of time with the data for the reference winding in good insulative condition to thereby judge deterioration of said insulated article.

The foregoing object, other objects as well as specific construction and function of the method and the apparatus for checking the insulative condition in the insulated winding used in various electrical appliances according to the present invention will become more apparent and understandable from the following detailed description thereof, when read in conjunction with the accompanying drawing.

In the drawing:

FIGS. 1A and 1B are respectively graphical representations showing characteristic curves of deformation when external mechanical force is imparted to an insulated winding, in which FIG. 1A shows the deformation characteristic curve of a reference article in good insulative condition, and FIG. 1B shows that of an insulated winding of deteriorated insulation;

FIGS. 2A and 2B respectively show accelerometer output versus natural frequency characteristic curves of the insulated winding, in which FIG. 2A illustrates a case of a reference winding in good insulative condition, while FIG. 2B denotes a case of an insulated winding with deteriorated insulation;

In the following, one preferred embodiment of the present invention will be explained in reference to the accompanying drawing.

Figure 1A:
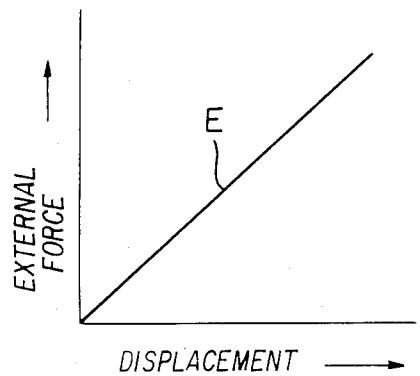
Figure 1B:
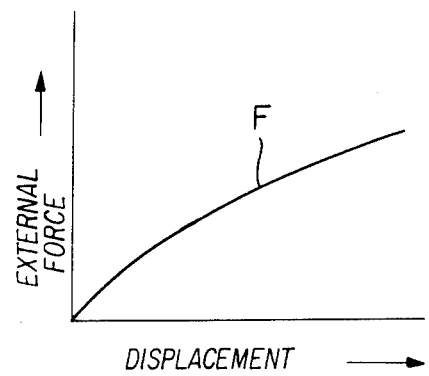

Reference is first made to FIGS. 1A and 1B which show respectively deformation characteristics when the external mechanical force is applied to the insulated winding. This external mechanical force may be either a tensile load or a bending load. When the insulation is satisfactory, it indicates a rectilinear deformation characteristic as shown by the characteristic line E in FIG. 1A. However, in the case where the insulation becomes deteriorated over the years, the external mechanical force indicates a non-linear characteristic as shown by the characteristic line F in FIG. 1B.

Figure 2A:
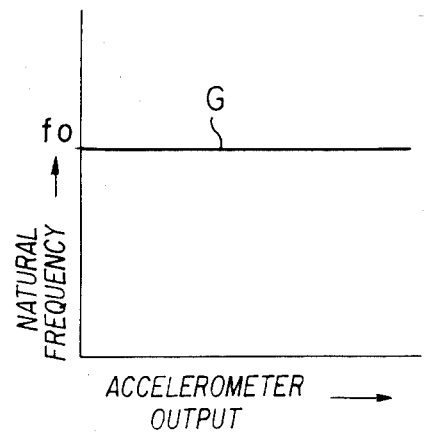

Accordingly, when the condition of the insulated winding is satisfactory, the natural frequency of the insulated winding, when it vibrates, does not depend on magnitude of the applied vibration as shown by the characteristic line G in FIG. 2A, but it assumes a certain definite value $f_0$. However, when the insulation becomes deteriorated, the natural frequency becomes lower than $f_0$ as shown by the characteristic line H in FIG. 2B, and it tends to be lower as the accelerometer output increases.

Figure 2B:
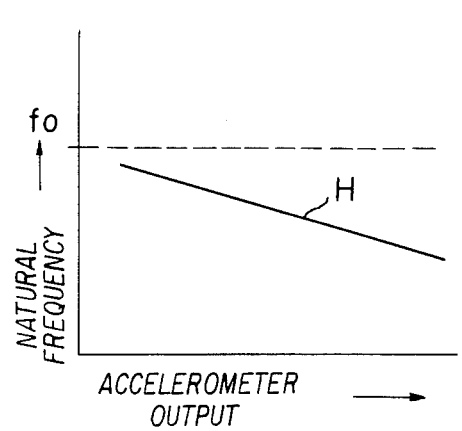

From the abovementioned standpoint, it becomes possible to examine the deterioration of the insulated winding, etc. by detecting the accelerometer output versus natural frequency characteristic of the insulated winding as shown in FIGS. 2A and 2B. This is the principle of the insulation checking method according to the present invention. In more detail, the condition of the insulated winding can be determined by first applying external mechanical force to the insulated winding for its examination, then measuring the accelerometer output and the natural frequency in the insulated winding at that time, and detecting variations in the natural frequency with respect to variations in the accelerometer output.

Figure 3:
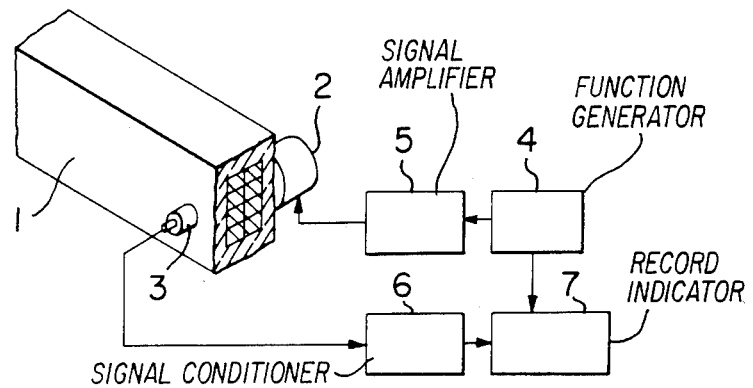
FIG. 3 is a schematic constructional diagram to illustrate the insulation checking method for the insulated winding according to one embodiment of the present invention, wherein an external force is applied to an insulated winding by an exciting (vibrating) force applying device.

FIG. 3 is a schematic constructional diagram showing the insulation checking method according to one embodiment of the present invention, wherein a reference numeral (1) designates an insulated winding for a rotary electric machine, etc., to one lateral surface part of which a vibration applying device (2), with its frequency being made continuously variable, is attached so as to impart the external force to the insulated winding. A numeral (3) refers to an accelerometer mounted on the other lateral surface of the insulated winding (1) opposite to the vibration applying device (2). A vibration applying signal generated from a function generator (4) is amplified in a signal amplifier (5) with a certain definite value, and the insulated winding (1) is excited by the vibration applying device (2). The accelerometer output to the insulated winding (1) is detected by the pick-up (3), and, after its amplification, comparison, and rectification in an signal conditioner (6), an acceleration signal is forwarded to a record indicator (7). To this record indicator (7), there is also forwarded a signal from the function generator (10). While the exciting frequency from the function generator (4) is being continuously varied, the accelerometer output signal forwarded from the signal conditioner (6) reaches a maximum. This is called the resonant point, and a signal forwarded from the function generator (4) at that time indicates the natural frequency. In this way, the natural frequency with respect to the accelerometer output becomes known. Next, the degree of amplification of the signal amplifier (5) is varied to obtain similar data. By repeating these operations over several stages, the accelerometer output versus natural frequency characteristic as shown in FIG. 2 becomes clarified and the deterioration in the insulative condition can be checked.

Figure 4:
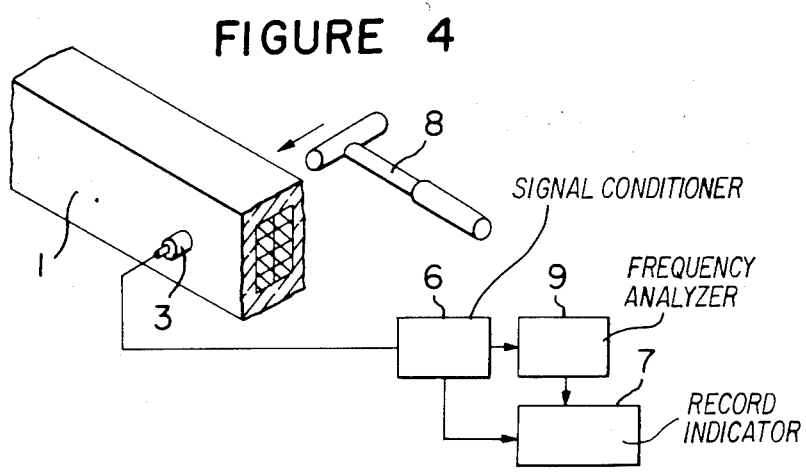
FIG. 4 is a schematic constructional diagram showing the insulation checking method for the insulated winding according to another embodiment of the present invention, wherein an external force is applied by a hammer.

FIG. 4 shows another schematic constructional diagram for explaining the insulative condition checking method according to another embodiment of the present invention, wherein the insulated winding is hit by a hammer to impart thereto an external mechanical exciting force in a pulsive form. When the insulated winding (1) is hit by a hammer (8), a speed acceleration signal is detected by the accelerometer (3) attached to the surface of the insulated winding (1) opposite to the hammer (8). This speed acceleration signal is amplified by the signal conditioner (6) and forwarded to a frequency analyzer (9). In the frequency analyzer (9), the natural frequency is found by analyzing a signal level for each frequency, and then this detected signal is forwarded to the record indicator (7). Into this record indicator (7), a signal from the signal conditioner (6) has also been sent, whereby the natural frequency with respect to the accelerometer output is found. Next, by varying the percussive force of the hammer (8), there may be found the natural frequency with respect to a different accelerometer output. By repeating this procedure several times, there can be obtained the accelerometer output versus natural frequency characteristic as shown in FIG. 2, whereby the state of deterioration in the insulative condition can be checked.

In the above-described embodiment, deterioration in the insulative condition has been determined by the inspecting personnel who sights the displayed contents of the accelerometer output versus natural frequency characteristic with his naked eyes. However, a more objective determination can be done when the checking device is provided with dual functions of operation and determination.

Figure 5:
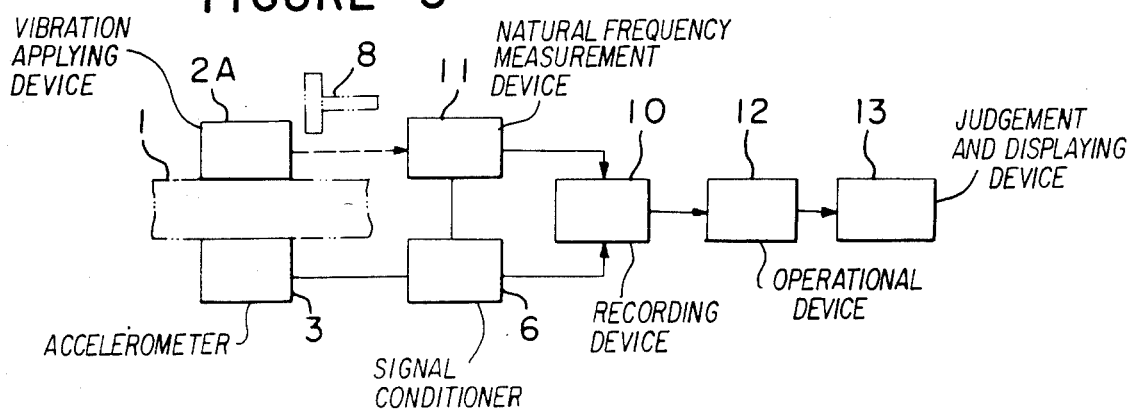
FIG. 5 is a schematic constructional diagram showing the insulation checking method for the insulated winding according to still another embodiment of the present invention.

FIG. 5 is a block diagram showing a construction of a different embodiment according to the present invention which incorporates the abovementioned dual functions in the checking device. A vibration which had been detected by the accelerometer (3) is put in the signal conditioner (6) and amplified therein, after which the amplified signal is sent into a recording device (10) and a natural frequency measurement device (11). When an exciting force signal is required for measuring the natural frequency, a signal from the vibration applying device (2A) is also put in the natural frequency measuring device (11). Then, the signals from the natural frequency measuring device (11) and the signal conditioner (6) are received by the recording device (10), after which the natural frequency relative to the accelerometer output is sent into an operational device (12) as the operational data. The operational device (12) stores therein the input data one after another, and by finding a value of the natural frequency or variations in the natural frequency with respect to variations in the accelerometer output, as measured from the characteristics shown in FIGS. 2A and 2B, it compares the input data with those of the reference article in good insulative condition which were previously stored therein, determines the deterioration in the insulative condition of the insulated article as an object of measurement, and displays the result of the determination in a display device (13). The external mechanical force for excitation of the insulated winding can be done by either the vibration applying device 2A or the hammer (8).

Incidentally, the insulative condition checking method according to this embodiment is directed, to checking the insulated article by the measurement of variations in the characteristics as shown in FIGS. 2A and 2B. The construction of the device for the measurement is not limited to each of the above-described embodiments, but various other constructions may be adopted.

Furthermore, these embodiments of the present invention are not only directed to the insulated winding of the rotary electric machines, but also can be applied to the insulated winding for stationary devices.

As stated in the foregoing, since the embodiments according to the present invention are so constructed that an external mechanical force for excitation is imparted to the insulated winding, the accelerometer output and the natural frequency are then measured, and variations in the natural frequency with respect to variations in the accelerometer output or values of the natural frequency are detected to thereby determine deterioration in the insulated article, a quantitative checking of the deterioration in the insulative condition can be effected at a position where the measurement is to be made, without the application of high tension voltage or causing damage to the insulated winding.

Figure 7A:
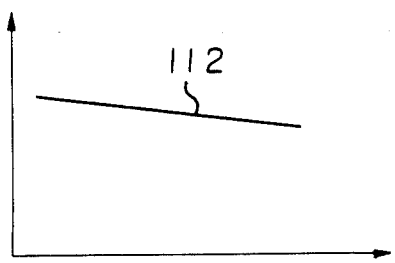
FIGS. 7A and 7B are comparative characteristic diagrams of amplitude of acceleration of vibration for explaining other embodiment of the present invention.
Figure 7B:
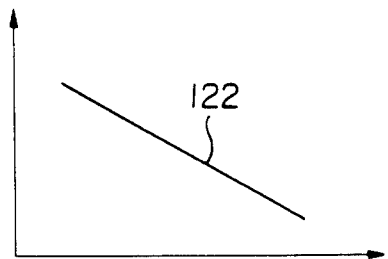
Figure 8:
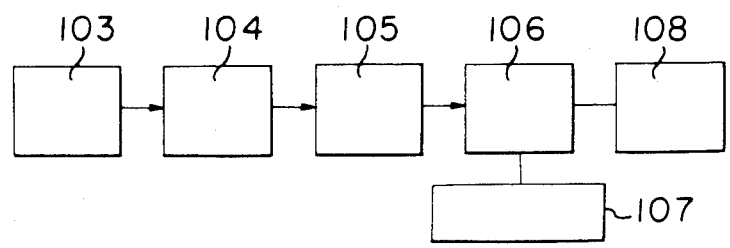
FIG. 8 is a wiring diagram for one embodiment of the insulation checking device according to the present invention.

FIGS. 6 to 8 inclusive illustrate further embodiments of the present invention.

Figure 6A:
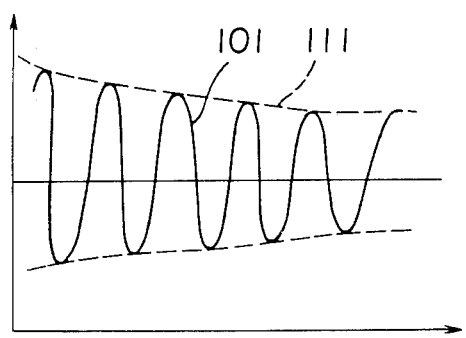
FIGS. 6A and 6B are comparative characteristic diagrams for acceleration of vibration for explaining other embodiment of the present invention.
Figure 6B:
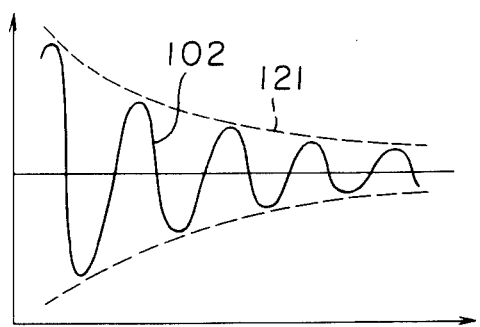

FIGS. 6A and 6B illustrate changes with lapse of time in the measurement quantities such as the acceleration of vibration, vibration speed, vibration displacement, sound pressure, and others, when the surface of the insulated winding is hit by the hammer, or like other percussion device. For the sake of simplicity, explanations hereinafter will be made, in particular, with the acceleration of vibration as the object. When the insulated winding in good insulative condition is hit with a hammer, etc., its acceleration of vibration indicates a gentle attenuation with lapse of time, as shown by a solid line (101) in FIG. 6A. In contrast to this, when the insulated winding is in a deteriorated condition, there is seen an abrupt damping in the acceleration of vibration due to friction among lamellar voids generated in the resulting material as shown by a solid line (102) in FIG. 6B. Difference between these two damping ratios may be more clearly understood from the enveloping lines as shown by dash lines (111), (121) in FIGS. 6A and 6B. Also, by processing the signals of the accelerometer output as measured, the damping ratio can be illustrated as shown in FIGS. 7A and 7B in an amount corresponding to one half of the enveloping line of the accelerometer output, i.e., with the amplitude of the accelerometer output being on the axis of ordinate in the logarithmic representation. According to this method of illustration, the damping characteristic can be represented generally by a rectilinear line, and the damping ratio can be found from a degree of inclination of the straight line, hence the ratio can be compared quantitatively. That is to say, by making comparison between inclination of the rectilinear line (112) in FIG. 7A showing the characteristic of the insulated winding in good insulative condition and inclination of the rectilinear line (122) in FIG. 7B showing the characteristic of the insulated winding in a deteriorated insulative condition, a degree of deterioration in the insulated winding with an impoverished quality with respect to that of good quality can be evaluated quantitatively.

The method and the apparatus of the present invention are to examine various insulated articles to find out deterioration in their insulative condition by taking waveforms of the acceleration of vibration in a pattern as shown in FIGS. 6A and 6B, or by finding inclination of rectilinear lines as shown in FIGS. 7A and 7B.

In these two methods as mentioned above, the final judgement on deterioration in the insulated articles as compared with the reference article in good condition should be done by the inspecting personnel. However, by use of the checking device having both functions of operation and judgement, objective checking on the deterioration becomes further possible.

FIG. 8 illustrates one embodiment of such checking device, which is constructed with an amplifier (104) for amplifying signals from a measuring element (103) for detecting acceleration of vibration, a damping ratio measuring device (105), a data storage device (107) for storing therein data for the damping ratio in the insulated article in good insulative condition, an operating device (106), to which are applied an output from the damping ratio measuring device (105) and an output from the data storage device (107) storing therein the data of the damping ratio of the insulated article in good insulative condition, and a judgement and display device (108).

By the abovementioned construction, the signal from the measuring element (103) as amplified by the amplifier (104) is introduced as an input into the damping ratio measuring device (105) for obtaining an damping ratio. The data of the damping ratio are introduced as inputs into the operational device (106) together with the data of the damping ratio in the insulated article in good insulative condition, where the comparison and operations are carried out on both input data. If a rate of increase in the damping ratio of the insulated article as measured exceeds a permissible preset value, the judgement and display device (108) informs the inspecting personnel of the deterioration in the insulative condition of the article as measured. In this manner, the inspecting personnel is able to obtain judgement on the deterioration in the insulative condition of the insulated article by a single operation of giving a hammer strike onto a predetermined portion of the insulated article to be measured. In the foregoing, explanations have been given paying all attention to the acceleration of vibration. It should, however, be noted that, in case of detecting changes in the frequency behavior with lapse of time, the same resulting effect can be obtained with the vibration speed, the vibration displacement, or the sound pressure, as the object.

In passing, the embodiment of the present invention as described above does not necessarily rely on the methods as shown in FIGS. 6A, 6B and FIGS. 7A, 7B for obtaining the damping ratio as the changes in the frequency behavior with lapse of time. In short, its characteristic point resides in checking deterioration in the insulative condition of the insulated article by comparting the changes in the frequency behavior or the sound pressure with lapse of time with the characteristics of the reference article in good insulative condition.

As mentioned in the foregoing, the embodiments according to the present invention are capable of checking deterioration in the insulative condition of the insulated articles by arbitrarily setting a portion for the measurement and without necessity for applying an electric potential to the insulated article and without causing any damage thereto.

We claim:

1. A method for testing the condition of the insulation in an insulated winding, comprising the steps of:
   applying an external mechanical force to said insulated winding so as to impart a vibration having a frequency in said insulated winding;
   measuring said frequency in said insulated winding;
   measuring the amplitude of said vibration in said insulated winding with an accelerometer to produce an output;
   detecting a change in said frequency with respect to a change in said accelerometer output;
   determining the condition of said insulation based on said change in frequency.

2. The method for testing according to claim 1 wherein:
   said external mechanical force is the output of a vibration applying device driven by an excitation signal from a functional generator;
   said accelerometer output is received and amplified by a signal conditioner to produce an amplified signal;
   said excitation signal and said amplified signal being received by a recording and displaying device; and further comprising the step of:
   varying said excitation signal so as to obtain a series of values of said frequency as a function of said amplified signal from said recording and displaying device.

3. The method for testing according to claim 1 wherein:
   said external mechanical force is a hammer strike;
   said accelerometer output is received and amplified by a signal conditioner to produce an amplified signal;
   said amplified signal is analyzed by a frequency analyzer to detect said frequency;

said frequency and said amplified signal being received by a recording and displaying device; and
further comprising the step of:
varying the force of said hammer strike so as to obtain a series of said values of said frequency as a function of said amplified signal from said recording and displaying device.

4. The method for testing according to claim 1, wherein:
said accelerometer output is received and amplified by a signal conditioner to produce an amplified signal;
said amplified signal is measured by a frequency measuring device to detect said frequency;
said frequency and said amplified signal being received by a recording device; and further comprising the steps of:
storing in an operational device data from said recording device concerning said frequencies and said amplified signals;
displaying the results of said determination of said insulation in a displaying device.

5. The method for testing according to claim 2 further comprising the steps of:
storing in an operational device data from said recording and displaying device concerning said excitation signal and said amplified signal.

6. The method for testing according to claim 3 further comprising the step of:
storing in an operation device data from said recording and displaying device concerning said value and said amplified signal.

* * * * *